US012648871B2

(12) United States Patent
Skelton

(10) Patent No.: US 12,648,871 B2
(45) Date of Patent: Jun. 9, 2026

(54) ADJUSTABLE FINGER SPLINT

(71) Applicant: Andrew C. Skelton, Austin, TX (US)

(72) Inventor: Andrew C. Skelton, Austin, TX (US)

( * ) Notice: Subject to any disclaimer, the term of this patent is extended or adjusted under 35 U.S.C. 154(b) by 25 days.

(21) Appl. No.: 18/716,730

(22) PCT Filed: Jan. 12, 2022

(86) PCT No.: PCT/US2022/012123
§ 371 (c)(1),
(2) Date: Jun. 5, 2024

(87) PCT Pub. No.: WO2023/136816
PCT Pub. Date: Jul. 20, 2023

(65) Prior Publication Data
US 2025/0032299 A1 Jan. 30, 2025

(51) Int. Cl.
*A61F 5/058* (2006.01)
(52) U.S. Cl.
CPC ................................ *A61F 5/05875* (2013.01)
(58) Field of Classification Search
CPC .... A61F 5/05875; A61F 5/0118; A61F 5/013;

A61F 5/10; A61F 2005/0172; A61F 2005/0179; A61F 5/05866; A61F 2007/0037; A61F 13/10; A61F 13/104; A61F 13/107
See application file for complete search history.

(56) References Cited

U.S. PATENT DOCUMENTS

| | | | |
|---|---|---|---|
| 5,038,764 A | 8/1991 | Paez | |
| 5,328,448 A | 7/1994 | Gray et al. | |
| 5,681,269 A | 10/1997 | Basaj et al. | |
| 6,502,577 B1 | 1/2003 | Bonutti | |
| 2020/0390583 A1 * | 12/2020 | Skelton | ................... A61F 5/013 |

OTHER PUBLICATIONS

PCT Search Report and Written Opinion mailed Oct. 31, 2022 for PCT application No. PCT/US2022/012123, 18 pages.

* cited by examiner

*Primary Examiner* — Ophelia A Hawthorne
(74) *Attorney, Agent, or Firm* — Lee & Hayes, P.C.

(57) ABSTRACT
An adjustable finger splint having a main body and slide. The slide configured to move relative to the main body to apply variable pressure to an injured finger to cause the injured finger to extend or straighten. The main body is movably coupled to a palmar support and at least a portion of a finger cradle to support the palm and metacarpophalangeal joint during use.

20 Claims, 10 Drawing Sheets

ADJUSTABLE FINGER SPLINT

CROSS-REFERENCE TO RELATED APPLICATION(S)

This application is a U.S. national stage application under 35 USC § 371 of International Application No. PCT/US22/12123 filed on Jan. 12, 2022 and entitled "ADJUSTABLE FINGER SPLINT," the entire contents of which is incorporated herein by reference.

BACKGROUND

A human hand has numerous bones, including phalanges and metacarpals. Each finger has three phalanges: a proximal phalange, an intermediate phalange, and a distal phalange. A thumb has two phalanges. Phalanges are hinged together with interphalangeal joints. For example, a finger's proximal phalange and intermediate phalange are joined by a proximal interphalangeal (PIP) joint, while a finger's intermediate phalange and distal phalange are joined by a distal interphalangeal (DIP) joint. A finger's proximal phalange is joined to a metacarpal with a metacarpophalangeal (MCP) joint.

Unfortunately, accidents or other medical conditions can impact the flexion and/or extension of a finger's interphalangeal joints. For example, when a tendon used to extend a finger becomes torn while another tendon used to pull the finger toward the palm of the hand remains intact, the finger can become contracted against the palm. Treatment of such an injured finger can involve bracing the finger into a desired position while the finger heals. Some devices have been developed that use screws to move parts into place to brace an injured finger. However, conventional devices fail to achieve sufficient magnitude of force or rigidity on the finger.

BRIEF DESCRIPTION OF THE DRAWINGS

The detailed description is set forth with reference to the accompanying figures. In the figures, the left-most digit(s) of a reference number identifies the figure in which the reference number first appears. The use of the same reference numbers in different figures indicates similar or identical items or features.

DETAILED DESCRIPTION

Figure 1:
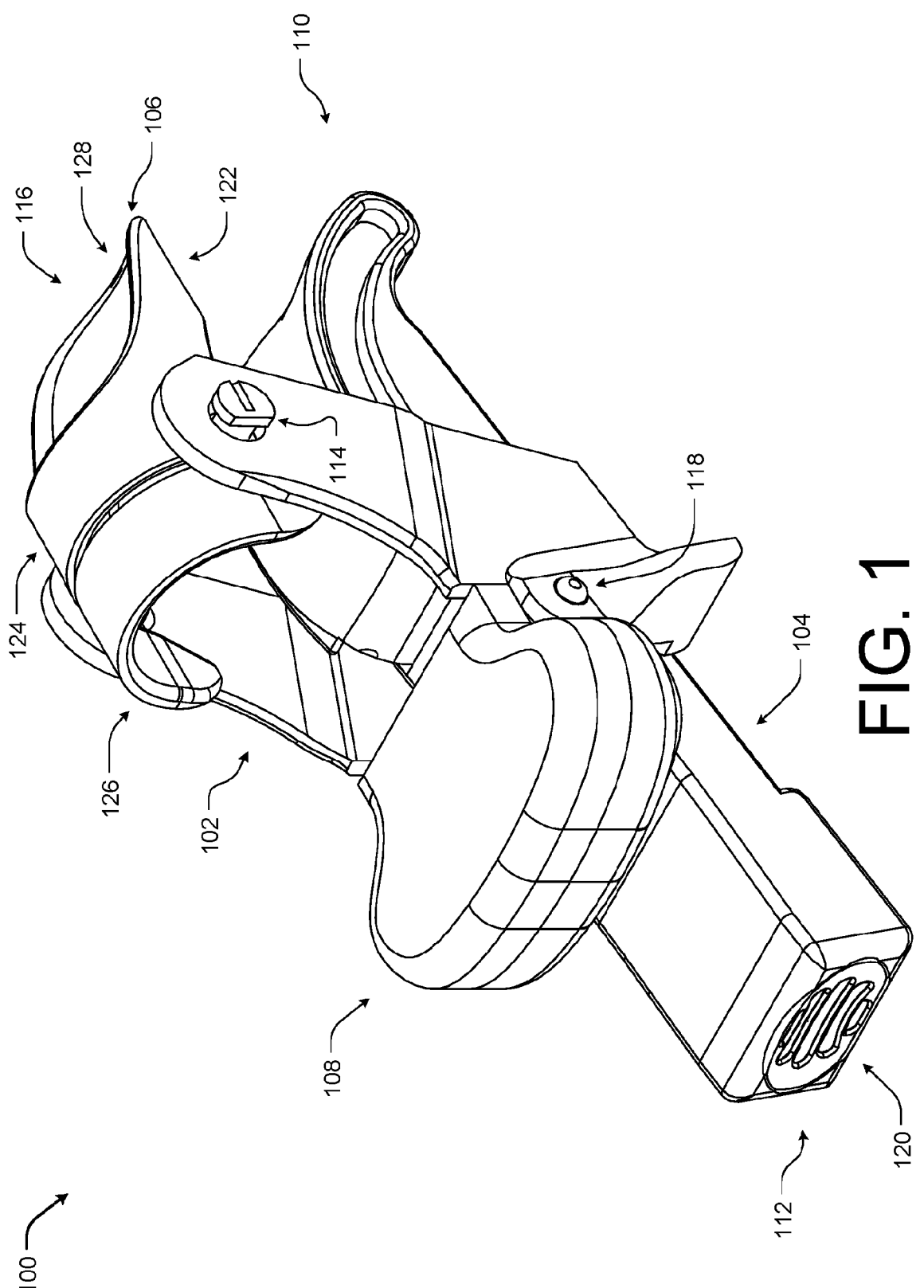
FIG. 1 depicts an embodiment of an adjustable finger splint according to some implementations.

This disclosure includes systems and implementations for providing an adjustable finger splint usable to treat various finger related injuries. For example, age, injury, or damage to one or more of the figures may cause the fingers to stiffen or lock in a bent or flexed position. For instance, damage or injury to the extensor tendons or ligaments in the finger often cause the finger to lock in a bent or flexed position due to force exerted by the flexor tendons on the finger. In this instance, if the injury remains untreated, the finger may remain permanently in a flexed position. However, conventional treatments including casting the finger locks the finger in an extended position for long periods of time. Therefore, the adjustable finger splint discussed herein provides for a splint that allows the user to remove the finger from the splint when the user's pain threshold is elapsed, as well as for the user to self-adjust the amount of pressure applied by the splint at any time during use, thereby, allowing the injury to be treated without the need for continuous casting or long recovery times due to surgery.

In some cases, the adjustable finger splint may include a self-contained unit or may be formed as an assembly of multiple separate components. For example, the adjustable finger splint may include a main body that may be permanently or releasably coupled to a slide. The main body may be hingably or rotationally coupled to a palmar support and/or a finger cradle. The main body may have a front end positioned away from the user during use and a rear end, opposite the front end, or positioned proximate to the user during use. When the finger is secured within the opening, the user's finger may be positioned such that the end of the user's finger is proximate the front end and the palm of the user is proximate the rear end.

The finger cradle may also include an opening or cavity configured to receive a finger of the user and to hold the finger in place during treatment or use. The finger cradle may be movable (e.g., rotatable) via the hinge coupling to the main body to ease the strain on an injured finger (e.g., fixedly bent finger) as the finger is inserted into the finger cradle. Likewise, the palmar support may be movable relative to the main body, such that during a finger insertion into the cradle, the palmar support may be hinged or moved away (e.g., downward) from the opening in the finger cradle to allow a larger area for accessing the opening, which is particularity beneficial for injuries in which the finger is immobilized or otherwise fixed in a bent position. After insertion, the palmar support may be rotated back (e.g., upwards) toward the finger cradle to thereby apply pressure or contact between the palmar pad affixed about the palmar support and the palm of the user.

A slide may be movable, adjustable, or slidable relative to the main body of the finger splint, and, thus movable, adjustable, or slidable relative to the injured finger held immobile by the finger cradle and palmar support. In these cases, the slide may be used to increase or decrease the pressure applied to the end of the finger by adjusting the position of the slide relative to the main body. In some implementations, the slide may have a wedge that is configured to apply increasing pressure on the end of the finger held within the main body as the slide is pushed or pulled outwards towards the front end of the main body. In this manner, as the slide is moved away from the body of the user, a curvature of the wedge forces the finger further and further toward a fully extended position. Thus, in some examples, the user may gradually reduce the angle of the injured finger relative to the hand (e.g., further straighten the finger) over a period of treatment (e.g., days, weeks, or months depending on the severity of the injury).

In some implementations, the slide may include a wedged head or front and a substantially linear back or rear. In some cases, the slide may be releasably coupled to the main body, such that the slide may be removed or separated from the main body when not in use and, thus, allow for the adjustable finger splint to be more easily stored or carried. In alternative implementations, the finger splint may be configured to prevent loss of the independent components of the splint and, thus while the palm side may be movable or adjustable with respect to the main body, the slide may be affixed, such as via a track and/or hinge, to the main body. In these alternative implementations, the slide and the main body may be inseparable. In either implementation, the slide may be retracted via the rear of the main body to allow the palmar support to move downward, increasing the access area for the opening in the finger cradle. In this manner, as the slide is returned or moved back through the main body, the slide may apply an upward force on the palmar support causing the palmar pad to contact the palm of the user, while substantially simultaneously, the wedged head of the side applies a pressure on the finger causing the finger to straighten. In some cases, the slide and/or the main body may be formed from a substantially rigid material, such as various plastics, polymers, metals, alloys, polyurethanes, gases, fluids, gels, foams, fibers, or combinations thereof.

As discussed above, the adjustable finger splint may include multiple substantially rigid components that apply pressure to an injured finger in a manner to hold the finger in a straightened or extended position. However, in some situations, direct contact between the substantially rigid material of the main body and slide of the splint may result in pain levels that exceeds the tolerance thresholds of the individual being treated, even for a short duration. Thus, the adjustable finger splint may also include a palmar pad atop the palmar support that together with the cradle design increases a comfort level of the user, preventing discomfort caused by the finger splint. In some cases, the palmar pad may be formed from a material, such as polyurethanes, elastomers, etc.

In some cases, injury to one or more fingers may be caused by age or be one of numerous injuries stained by the user. In these cases, the user may be unable to apply necessary force to the slide to cause the injured finger to extend. Thus, in some implementations, the adjustable finger splint may be designed, such that a third-party (e.g., physical therapist, hand therapist, doctor, surgeon, nurse, or other medical professional) is able to adjust the slide relative to the main body. In these implementations, the slide may include a pull or handle proximate to the front end that the third-party may use to adjust the slide relative to the main body. The main body may also include a grip or other stabilizing portion that the third-party may utilize to substantially maintain the position of the main body when adjusting the position of the slide. In one particular implementation, the main body may be weighted such that when the adjustable finger splint is set or rests on a table or other surface, the main body preserves its position as the palm side is moved.

In some cases, the finger splint may also be configured to allow the user or other medical professional to measure the angle of the finger relative to the hand of the user both at rest and during use of the splint. For instance, in some implementations, the adjustable finger splint may include a window such that the user or the medical professional may utilize a protractor or other tool to measure the relative angles between the finger and hand. In other implementations, the protractor may be built into the splint, such as printed along the window, or the main body may include an extended portion that may mirror the position of the finger within the opening of the main body. In still other implementations, the adjustable finger splint may include a dial that may be turned to adjust the position of the slide relative to the main body and also provide or determine the relative angle of the finger and hand.

FIG. 1 depicts an embodiment of an adjustable finger splint 100. The adjustable finger splint 100 may comprise a main body 102, a slide 104, a finger cradle 106, and a palmar support 108, as discussed above. As illustrated, the finger splint 100 may include a front 110 and a back 112. In the illustrated example, the front 110 is positioned away from the user during use and the back 112, opposite the front 110, is positioned proximate to or facing the body of the user during use.

Figure 3:
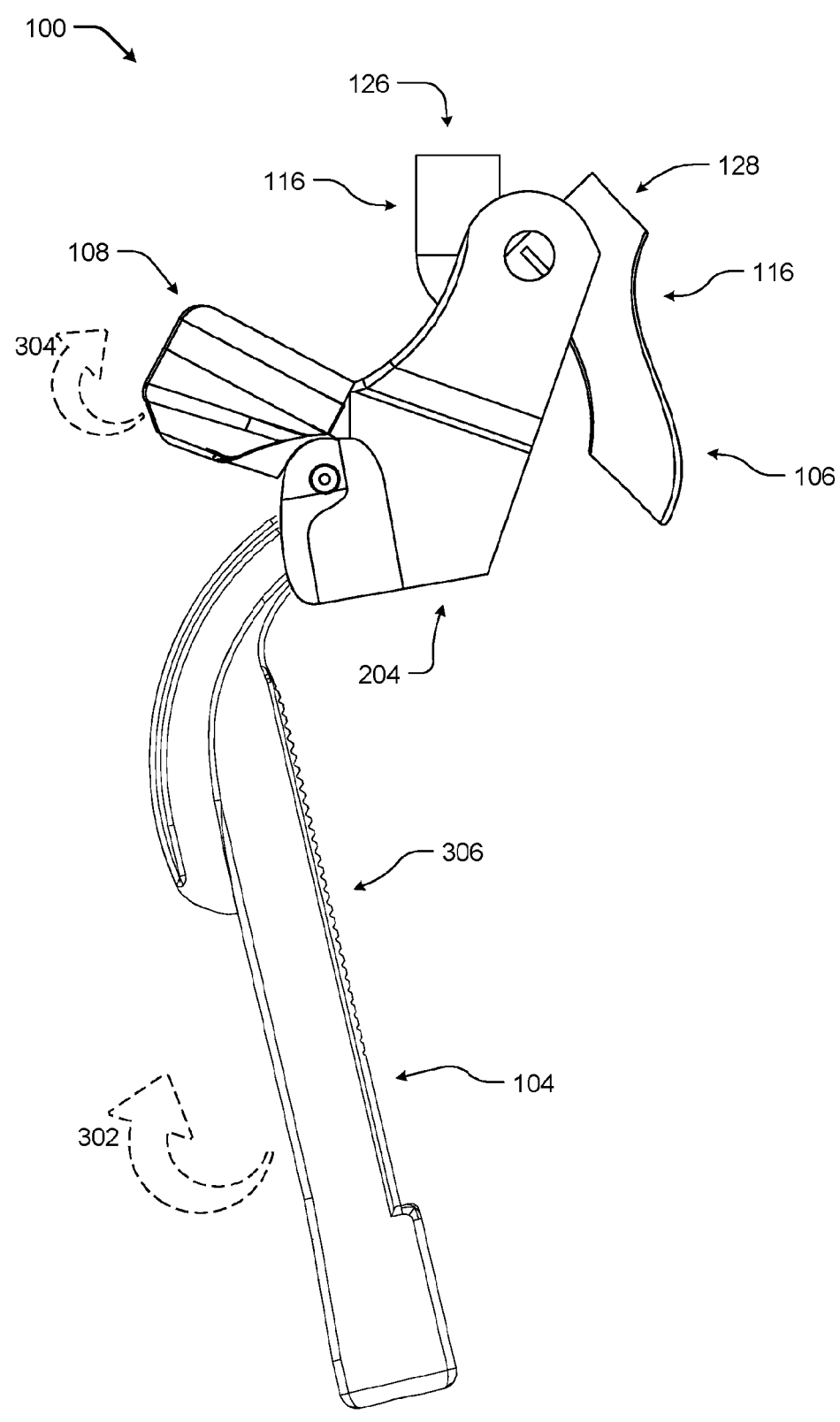
FIG. 3 depicts an example right side view of the adjustable finger splint as the slide is inserted into the main body according to some implementations.
Figure 5:
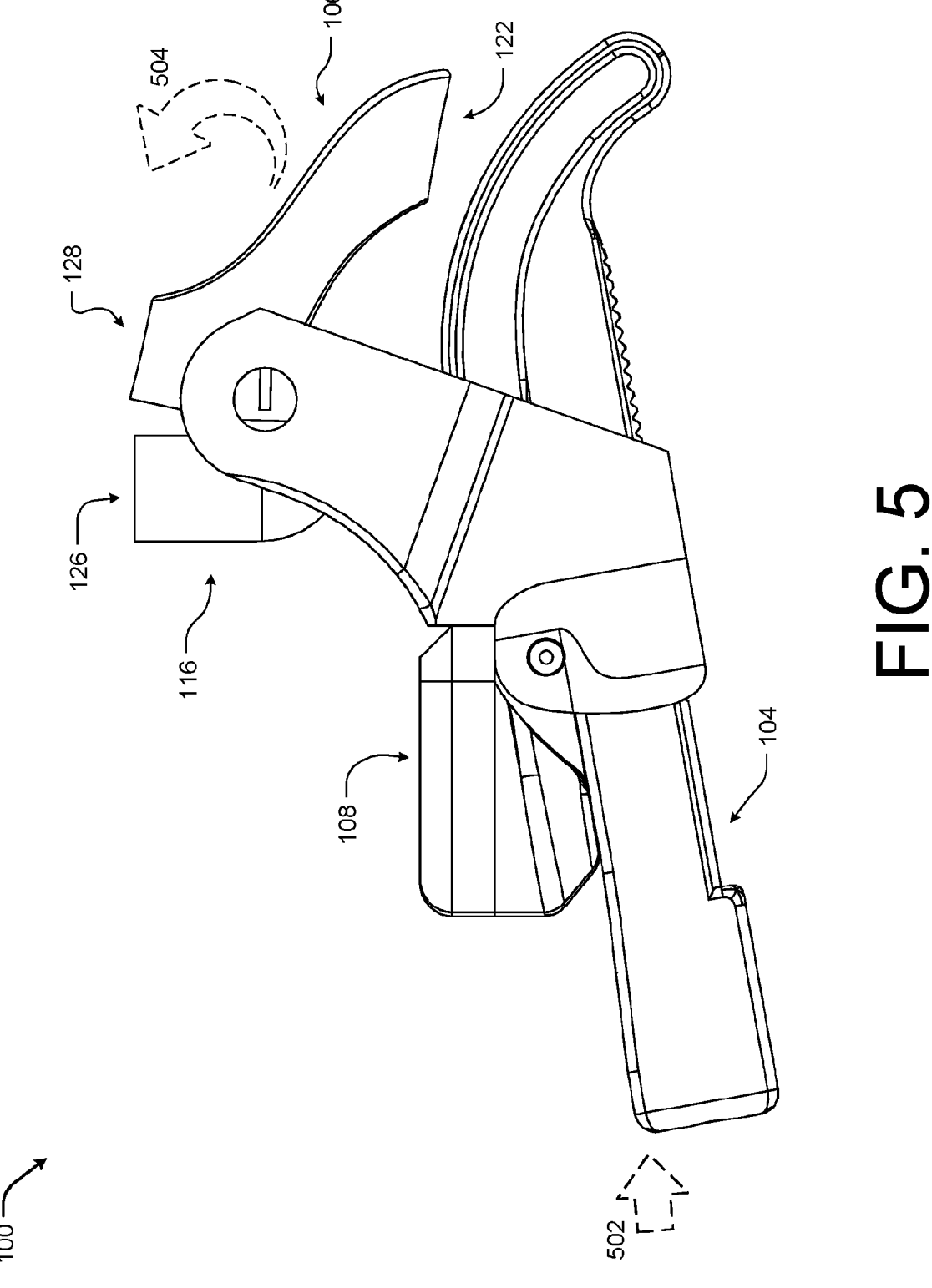
FIG. 5 depicts an example right side view of the adjustable finger splint as the slide is inserted into the main body according to some implementations.

As discussed above, the finger cradle 106 may include a back portion 126 that is coupled to and immobile with respect to the main body 102 and a front portion 128 that is hingably coupled to the main body 102 via hinges 114, such that the front portion 128 of the finger cradle 106 may transition between a first position, as illustrated in FIG. 3, and a second position, as illustrated with respect to FIG. 5. The finger cradle 106 may also include an opening or cavity, generally indicated by 116, through both the back portion 126 and the front portion 128 and configured to receive a finger of the user during treatment or use. As the front portion 128 may rotate downward with respect to the main body 102 and the back portion 126, a size of the opening 116 may be increased in a manner to allow the insertion of a fixedly bent finger. The palmar support 108 may also be hingably coupled to the main body 102 via hinges 118. Similar to the cradle 106, the palmar support 108 may transition between a first position and a second position, as illustrated with respect to FIG. 5.

In some cases, when the finger is secured within the finger opening 116, the user's palm may be resting on the palmar support 108, such that the end of the user's finger is proximate the front 110 and the palm of the user is proximate the back 112. The user may then push on a back end 120 of the slide 104, to cause the slide 104 to move in a direction towards the front 110 of the splint 100. The slide 104 may push on the finger of the user and/or a bottom surface 122 of the finger cradle 106 to cause the cradle 106 and the finger of the user to move slowly upwards as the slide 104 is moved towards the front 110. As the finger is extended upward, the finger cradle 106 moves upward or rotates about the hinges 114, while a top surface 124 of the cradle 106 applies a downward pressure on the finger causing the finger to straighten. In these examples, the position of the slide 104 relative to the main body 102 may be moved or adjusted to increase or decrease the pressure (e.g., upwards and downwards) applied to the end of the finger. In this manner, the user may set the pressure load based on the discomfort that the user is experiencing (e.g., by increasing the pressure, the effect of the treatment is increased but so is the discomfort) in real-time and during use.

In the illustrated example, the main body 102, the slide 104, the finger cradle 106, and the palmar support 108 are substantially rigid, such that the splint 100 may apply opposing pressure on a finger (via the slide 104, cradle 106, and the connection between the slide 104 and the cradle 106 via the main body 102) placed within the finger opening 116. However, in some situations, direct contact between the substantially rigid material and the finger may result in increased pain levels that exceeds the tolerance thresholds of the individual being treated, even for a short duration. Thus, in some implementations, the adjustable finger splint 100 may also include pads, such as a palmar pad to increase comfort and reduce pain caused by the finger splint 100 during use. For instance, in some cases, the cradle 106 may include a dorsal pad along an interior of the top surface 124. It should be understood that in other implementations, the pads may be optional or removable.

Figure 2:
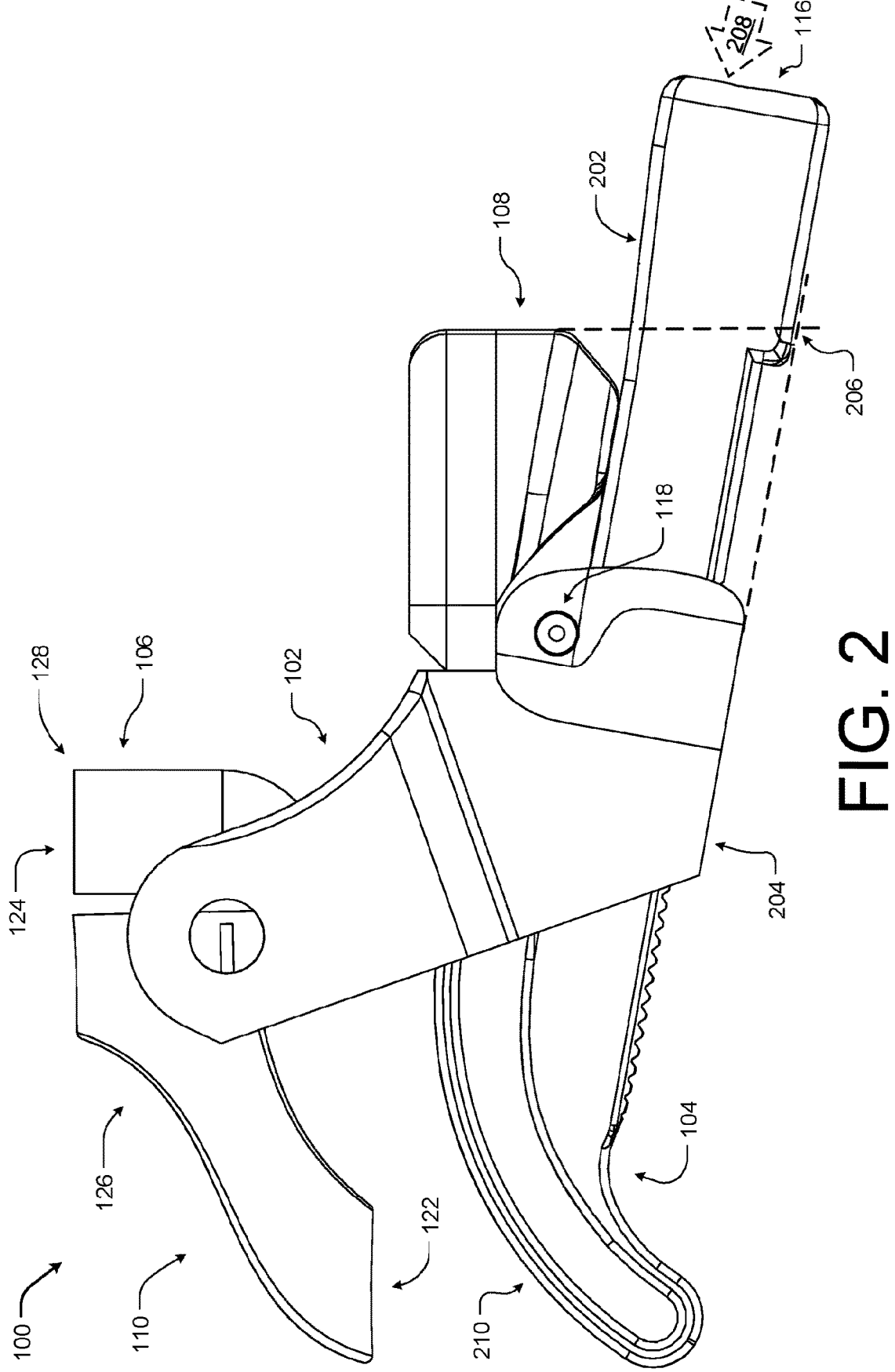
FIG. 2 depicts an example left side view of the adjustable finger splint of FIG. 1 according to some implementations.

FIG. 2 depicts an example left side view of the adjustable finger splint 100 of FIG. 1 according to some implementations. In the illustrated example, the finger splint 100 again includes multiple rigid or hard components, a main body 102, a slide 104, a finger cradle 106, and a palmar support 108. In this example, a finger of a user may be placed within the finger cradle 106 such that the palm of the user is resting on a pad associated with the palmar support 108. Accordingly, the palmar support 108 provides a metacarpophalangeal (MCP) platform that is configured to support the rear portion of the palm (in some cases, via a pad). In some cases, depending on the configuration of a top surface 202 of the slide 104, the palm of the user may be maintained in a fixed position during use (e.g., a substantially flat top surface 202) or adjusted as the slide 104 is moved forward through the main body 102 (e.g., a sloped top surface 202), as the slide 104 may provide upward pressure on the palmar support 108 during use. In this example, the palmar support 108 may rotate about the hinge 118 to increase the ease of finger insertion and/or to allow the slide 104 to be initially inserted between the main body 102.

In some case, during use, in addition to providing support for the palm via the palmar support 108, the finger of the user may contact an interior of a top surface 124 of the back portion 128 of the finger cradle 106 with a top surface of the finger behind (e.g., closer to the palm) the MCP joint and an interior of a bottom surface 122 of the front portion 126 of the finger cradle 106 with a bottom surface of the finger past (e.g., further from the palm) the MCP joint to provide support for the PIP joint of the user.

In the current example, the main body 102 may have a slide platform 204 extending between walls of the main body 102. The slide platform 204 may support the slide 104 during use and include a top surface (not shown) that is included at a predetermined angle relative 206 to the palmar support 108. The relative angle of the incline of the slide platform 204 to the palmar support 108 causes the slide 104 to engage the finger of the user in a manner that lifts the front end of the finger at an angle complementary to the relative angle 206 between the palmar support 108 and the slide platform 204. For example, the user may apply forward pressure 208 on the back end 116 of the slide 104 to cause a head portion 210 of the slide 104 to engage with the finger of the user. As illustrated when the slide 104 is engaged with the finger, the finger is raised upward toward cradle 106. Thus, in the engaged position, the top surface 124 of the back portion 128 of the cradle 106 applies a downward or stabilizing pressure on the proximal phalanx and the head portion 210 of the slide 104 applies an opposite upward pressure on the distal phalanx (or the end of the finger), causing the finger to extend as the MCP joint and the PIP joint are straightened. By maintaining force on the joint at maximum extension, the contracted tissues are elongated and mobility is restored. However, by allowing the user to apply the pressure 208 to the slide 104, the user is able to control the amount of time spent applying the treatment and, in some situations, to remove the hand from the splint 100, allowing the user use of the hand and a break from the treatment.

In the current example, the head portion 210 of the slide 104 has a wedged shape. The wedged shape may have a curvature that is configured to cause the finger to straighten as the slide 104 is pushed towards the front end 110 of the splint 100. Thus, in the illustrated implementation, the finger of the user is forced into the extended position in part due to the relative angle between the incline of the top surface of the slide platform 204 and the palmar support 108 and in part based on the curvature of the head portion 210 of the slide 104. The radius of the curvature of the head portion 210 is calibrated to maintain the DIP joint in a neutral position throughout the range of extension of the slide 104.

Figure 4:
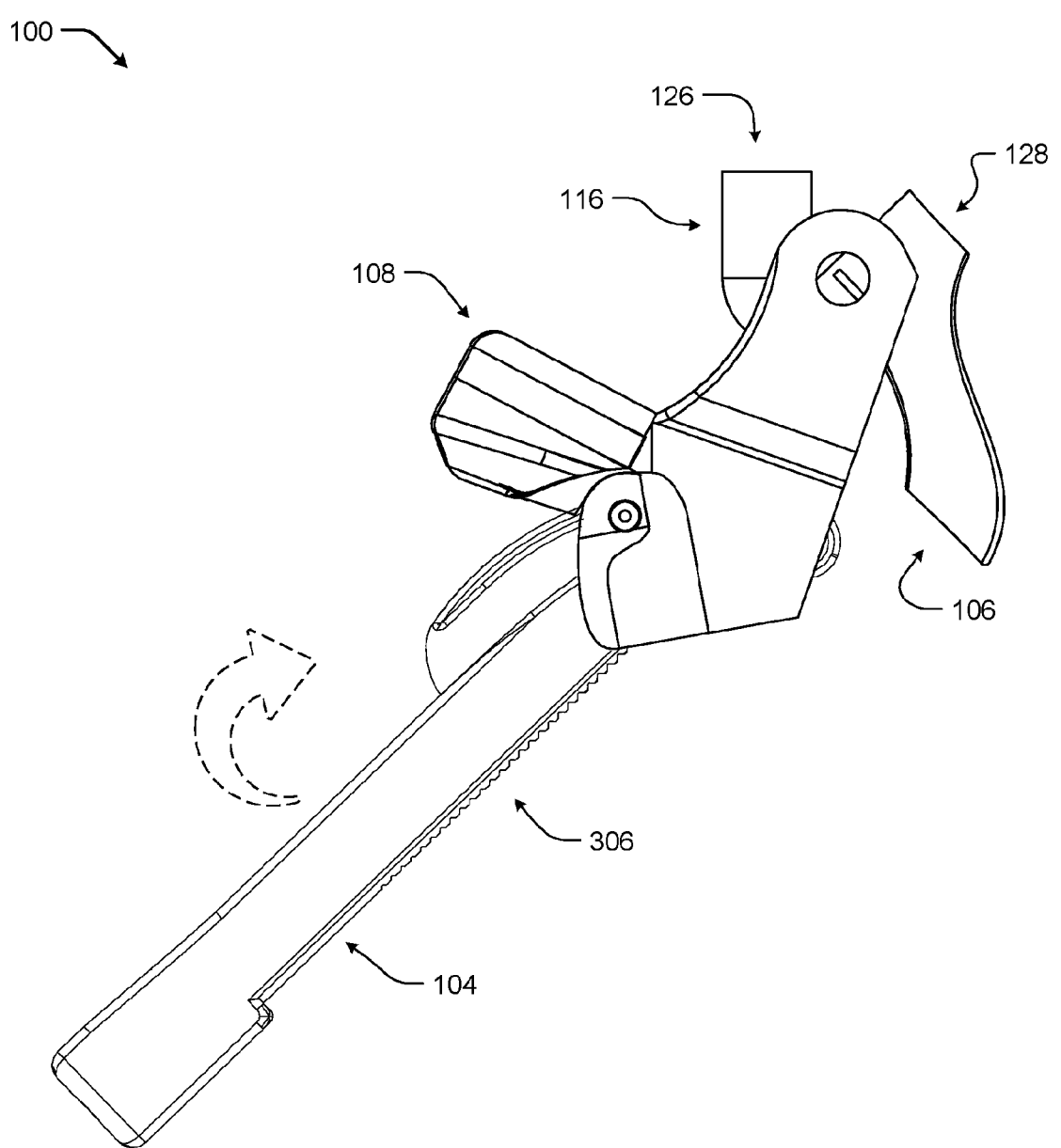
FIG. 4 depicts an example right side view of the adjustable finger splint as the slide is inserted into the main body according to some implementations.

FIGS. 3-5 depicts an example right side view of the adjustable finger splint 100 as the slide 104 is inserted into the main body 102. Initially, as shown in FIG. 3, the slide 104 is in an uninserted position. In this example, the user may insert a finger into the opening 116 of both the back portion 126 and the front portion 128 of the finger cradle 106. Once the finger is engaged, the user may rotate and move, as indicated by 302, the slide 104 upwards and into an opening 304 of the main body 102 as shown. As the slide 104 is rotated into position, the palmar support 108 may be moved upwards, as indicated by 304, to allow the slide room to engage a top surface of the slide platform 204. For example, the slide 104 may include notches, generally indicated by 306. The notches may be configured to engage with a top surface of the slide platform 204, such that a user may feel or count a number of notches the slide 104 has been inserted through the main body 102 and thereby monitor a treatment level during use.

With respect to FIG. 4, the user may continue to insert the slide 104 through the main body 102 as shown. In this example, the user may continue to rotate and move forward the slide 104, as indicated by 402. The slide 104 may engage through the opening of the main body 102 causing the notches 306 to engage with the top surface of the slide platform 204. With respect to FIG. 5, the slide 104 may be pushed through the opening of the main body 102, as indicated by 502, to engage a finger (not shown) to cause the finger and the front portion 128 of the cradle 106 to move upwards, as indicated by 504. The upward motion 504 of the finger and front portion 128 of the cradle 106 cause the back portion of the cradle 126 to apply a downward pressure on the finger between the MCP joint and PIP joint while the surface 122 and the head of slide 104 apply an upward pressure on the finger between the MCP joint and a fingertip of the finger. In this example, the palmar support 108 may be in a substantially horizontal position to provide support for the palm of the user during use.

Figure 6:
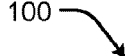
FIG. 6 depicts an example rear view of the adjustable finger splint of FIG. 1 according to some implementations according to some implementations.
Figure 6:
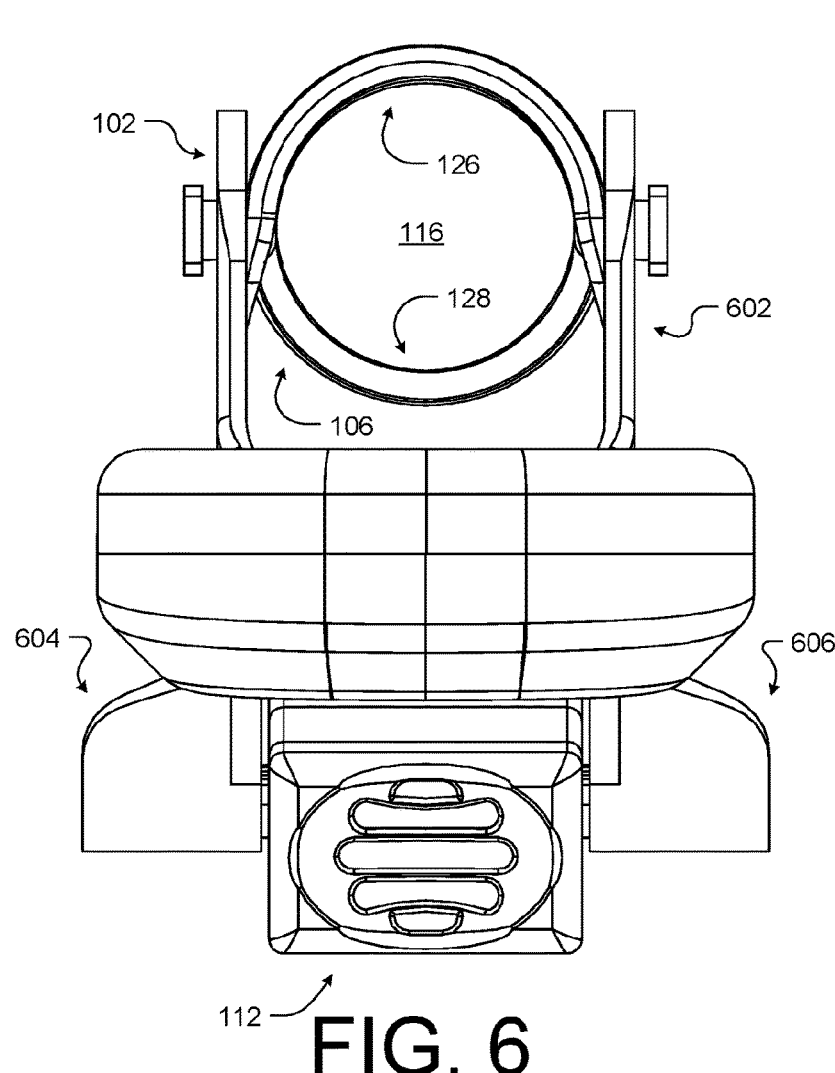

FIG. 6 depicts an example rear view of the adjustable finger splint 100 of FIG. 1 according to some implementations. As discussed above, the main body 102 includes a frame 602 that supports both the front portion 128 and the back portion 126 of the finger cradle 106. The front portion 128 and the back portion 126 of the finger cradle 106 forms a finger opening 116 to receive a finger of the user as discussed above. In the illustrated example, the finger cradle 106 does not include a pad, but it should be understood in other examples, either or both of the first portion 128 and/or the back portion 126 may include a dorsal pad secured or adhered to the interior surfaces of the finger cradle 106.

In the illustrated example, the back end 112 of the slide 104 may be textured or patterned to allow for increased friction when the user pushes or applies pressure to the back end 112 of the slide 104. It should be understood that the finger splint 100 may be operated by the user with one hand. For example, the user may grip a front (not shown) of the main body 102 using healthy fingers, generally at locations 604 and/or 606, while engaging the back end 112 of the slide 104 using the thumb.

Figure 7:
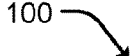
FIG. 7 depicts an example front view of the adjustable finger splint of FIG. 1 according to some implementations.
Figure 7:
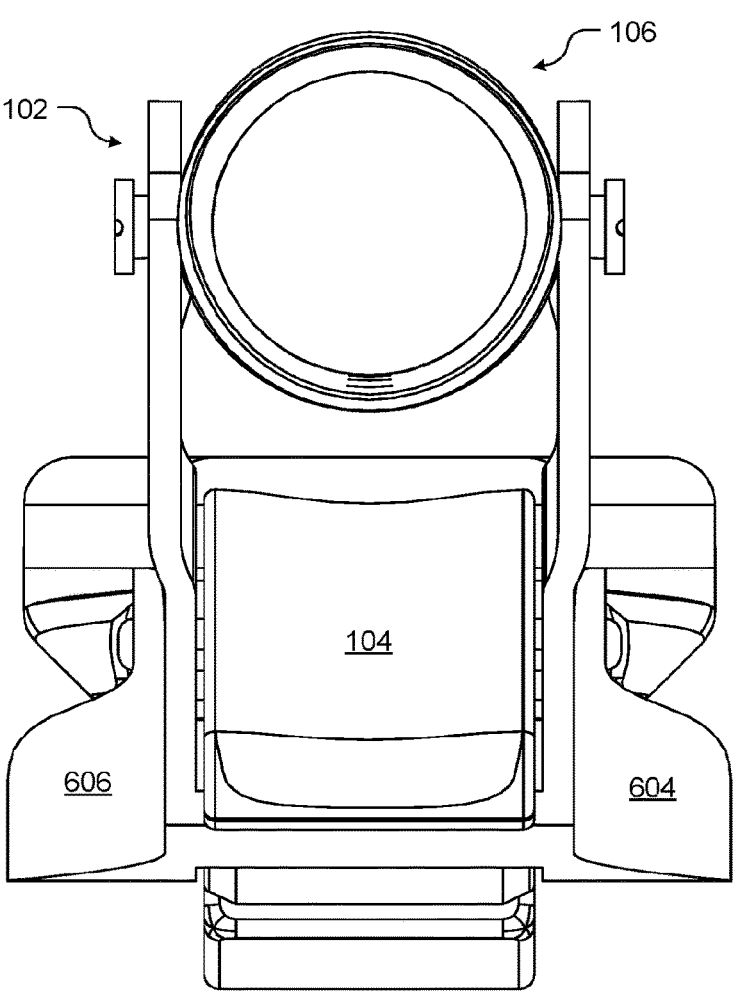

FIG. 7 depicts an example front view of the adjustable finger splint 100 of FIG. 1 according to some implementations. In the current example, the slide 104 is engaged with the main body 102. As illustrated, the cradle 106 is in an upright position to apply upward and downward pressure on a finger of the user, as discussed here. In this illustrated implementation and as discussed above, the user may place one or more healthy fingers at locations 604 and 606 to provide apply a backwards pressure when the user pushes the slide 104 forward. In some cases, the locations 604 and 606 may include a texture or grip that provides increased friction and allows the user to more easily apply the backwards pressure on the main body 102.

Figure 8:
FIG. 8 depicts an example top view of the adjustable finger splint of FIG. 1 according to some implementations.

FIG. 8 depicts an example top view of the adjustable finger splint 100 of FIG. 1 according to some implementations. In the current example, the slide 104 is currently in the at rest position and engaged with the main body 102, as in FIG. 7 above. As shown, the palmar support 108 include a palmar pad that may cover the surface of the support 108. Additionally, the front portion 128 and back portion 126 of the cradle 106 are shown in alignment, such as when a finger is held in a straight or extended position.

Figure 9:
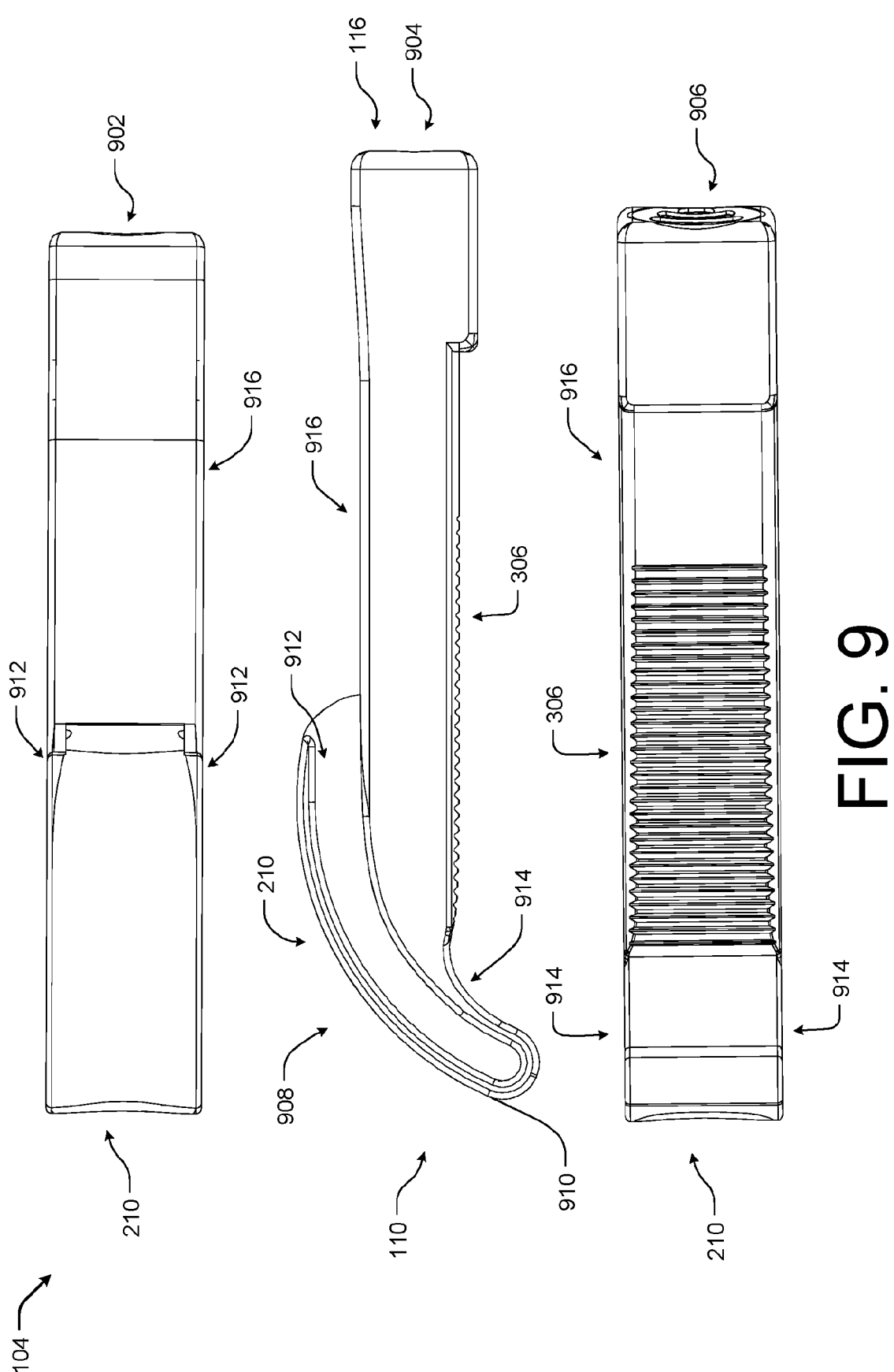
FIG. 9 depicts an example top view, side view, and bottom view of the slide of FIG. 1 according to some implementations.

FIG. 9 depicts an example top view 902, side view 904, and bottom view 906 of the slide 104 of FIG. 1 according to some implementations. As discussed above, in some implementations, the slide 104 may be releasably coupled to the main body 102 of FIGS. 1-8, such that the slide 104 may be removed or separated from the main body 102 when not in use and, thus, allow for the adjustable finger splint 100 to be more easily stored or carried. In the illustrated example, the slide 104 includes a slide rail 916 and a wedge shaped head 210 having a predefined curvature 908. The curvature 908 of the head 210 causes the finger to gradually extend or straighten as the slide 104 is moved in a direction towards the front end 110 of the splint 100. The curvature 908 having a radius of between approximately 3.0 centimeters (cm) and 5.0 cm. In one particular example, the radius of the curvature 908 may be 4.0 cm.

The head 210 also includes a lip or edge 910 that forms a groove or recessed portion 912 along either side of the slide 104. The main body (not shown) of the splint 100 may include two locking members that may be received into the recessed portion 912 via an opening 914 on either side of the slide 104. In some examples, the slide 104 may be coupled with the main body by placing the locking members into the recessed portion 912. Then, when the palmar support (not shown) is coupled to the main body over the slide 104, the palmar support prevents the slide 104 from decoupling from the main body during use. In this manner, the slide 104 is less likely to decouple or become lost.

In this example, the slide 104 may also include notches 306 that may be used to engage with the main body to assist with preventing the slide 104 from moving backward with respect to the main body during use. In some cases, the notches 306 may also assist the user with determining or estimating an input or insertion depth of the slide 104 into the main body. In this manner, the user may estimate progress associated with straightening a finger.

In some implementations, the length (e.g., the distance between a back end 116 and a front end 110) of the slide 104 may be between approximately 7.5 cm and 12.5 cm. The head 210 may also have a length that is between one-third and one-fourth the length of the slide 104 and the slide rail 916 may have length between two-third and three-fourths of the length of the slide 104. For example, the head 210 may be between 3.0 cm and 4.0 cm long and the slide rail 916 may be between 6.0 cm and 7.0 cm. The slide rail 916 may also have a height of between approximately 1.0 cm and 2.0 cm and a width between approximately 1.5 cm and 2.5 cm. The head 210 may have a height of between approximately 2.0 cm and 3.0 cm and a width between approximately 1.5 cm and 2.5 cm. In some cases, the width of the slide rail 916 and the head 210 may be the same or equal to the size of the slide opening in the main body, as discussed herein.

In some examples, the slide 104 may be formed as a single component or unit. The slide 104 may be formed from a rigid material, such as various plastics, polymers, polyethylene terephthalate, among others. In some cases, the slide 104 may have a shore D average hardness rating of between approximately 75 and 85.

In the current example, the slide 104 is illustrated as removed from the main body 102. However, it should be understood in other alternative implementations, the finger splint 100 may be configured to prevent the loss of the independent components of the splint 100 and, thus the palm slide 104 may be movable or adjustable with respect to the main body but affixed (e.g., via a track) to the main body 102, such that the splint 100 is a single unit.

Figure 10:
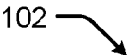
FIG. 10 depicts an example back perspective view of the main body of the adjustable finger splint of FIG. 1 according to some implementations.
Figure 10:
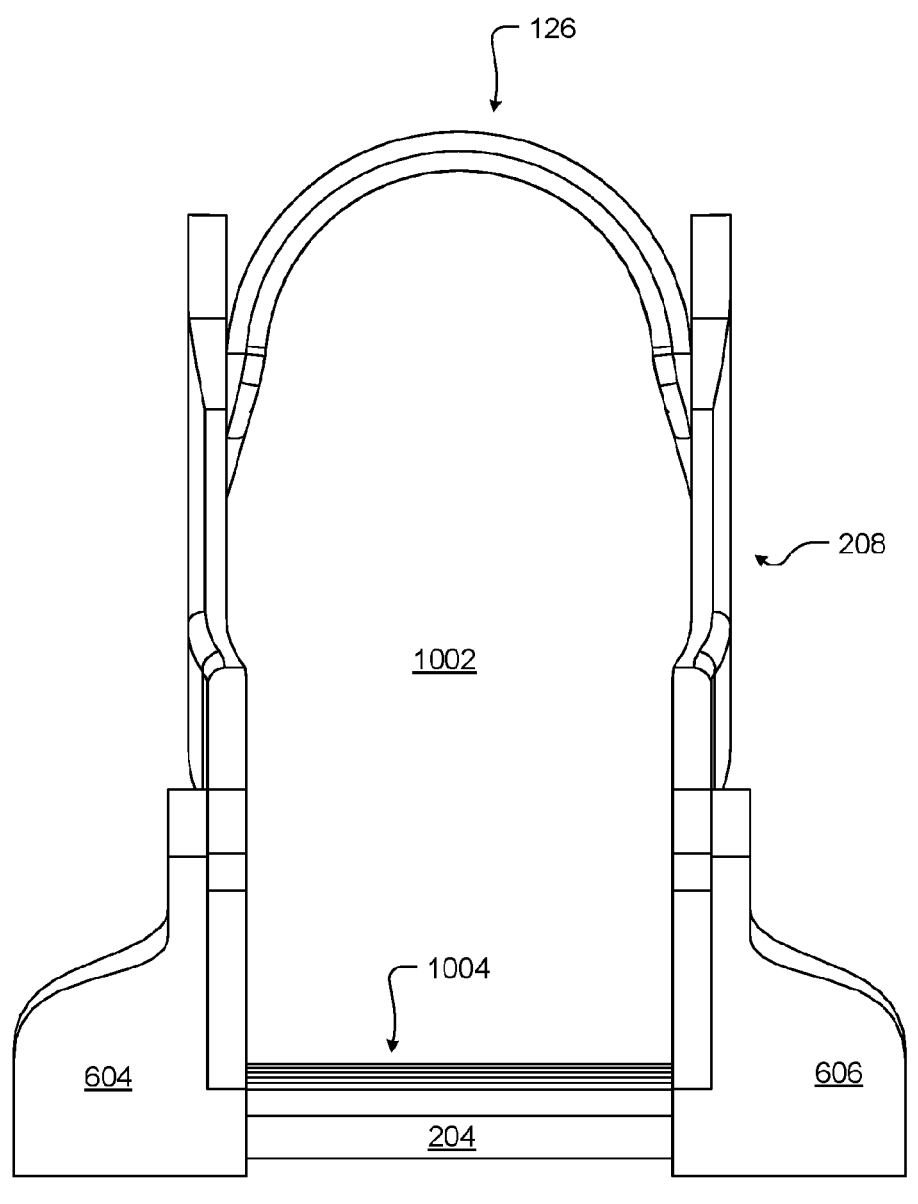

FIG. 10 depicts an example back perspective view of the main body 102 of the adjustable finger splint 100 of FIG. 1 according to some implementations. As discussed above, the main body 102 includes a frame 208 that is hingably coupled to both the front portion of the finger cradle (not shown) and the palmar support (not shown). The main body 102 may also be fixedly coupled to the back portion 126 of the finger cradle and to a slide platform 204, as shown. The space between the frame 208, the back portion 126 of the cradle, and the slide platform 204 may form an opening 1002 that may receive both a finger and the slide (not shown) during use.

The slide platform 204 may include a top surface 1004 that is also notched and configured to mate with the notches on the bottom surface of the slide to, thereby, prevent backwards motion or slipping during use. In some cases, the slide platform 204 is substantially horizontal, while in other cases, the slide platform 204 may include an incline. In this illustrated implementation and as discussed above, the side may also include locations 604 and 606 for the user to place one or more healthy fingers and to apply a backwards pressure when the user pushes the slide 104 forward. In some cases, the locations 604 and 606 may include a texture or grip that provides increased frictions and allows the user to more easily apply the backwards pressure on the main body 102.

In some examples, the main body 102, including the slide platform 204 and the back portion 126 of the finger cradle, may be formed as a single component or unit. The main body 102 may be formed from a rigid material, such as various plastics, polymers, polyethylene terephthalate, among others. In some cases, the main body 102 may have a hardness rating of approximately shore D average hardness rating of between approximately 75 and 85.

Although the subject matter has been described in language specific to structural features and/or methodological acts, it is to be understood that the subject matter is not necessarily limited to the specific features or acts described above. Rather, the specific features and acts described above are disclosed as example embodiments.

What is claimed is:

1. An adjustable finger splint comprising:
a main body including a frame, a back portion of a finger cradle, and a slide platform, the frame including a first side wall and a second side wall, the back portion of the finger cradle and the slide platform coupled between the first side wall and the second slide wall and defining a first opening for receiving a slide moveable with respect to the main body through the first opening;
a front portion of the finger cradle hingeably coupled to the first side wall and the second side wall of the frame, the front portion defining a second opening for receiving an injured finger; and
a palmar support hingeably coupled to the first side wall and the second side wall of the frame and defining a platform configured to support a palm of a user.

2. The adjustable finger splint as recited in claim 1, wherein, the palmar support is moveable downwards when the slide is removed from the first opening.

3. The adjustable finger splint as recited in claim 1, wherein, a pad is positioned over the palmar support.

4. The adjustable finger splint as recited in claim 1, wherein the slide platform includes one or more notches for engaging with the slide during use.

5. The adjustable finger splint as recited in claim 1, wherein the main body includes a first finger grip positioned to a first side of the first opening and a second finger grip positioned to a second side of the first opening, the first side opposite the second side.

6. The adjustable finger splint as recited in claim 1, wherein the back portion of the finger cradle includes a pad along at least a portion of an interior surface of the finger cradle.

7. The adjustable finger splint as recited in claim 1, wherein the front portion of the finger cradle is moveable within the first opening prior to a user inserting a finger into the adjustable finger splint.

8. The adjustable finger splint as recited in claim 1, wherein the palmar support defines a metacarpophalangeal platform.

9. An adjustable finger splint, comprising:
a main body defined by:
a frame having a first side wall and a second side wall;
a back portion of a finger cradle coupled between the first side wall and the second side wall; and
a slide platform coupled between the first side wall and the second side wall below the back portion of the finger cradle to define a first opening;
a front portion of the finger cradle movably coupled to the first side wall and the second side wall parallel to the back portion of the finger cradle, the front portion of the finger cradle defining a second opening and hingeably coupled to the first side wall and the second side wall of the frame;

a palmar support movably coupled to the first side wall and the second side wall and defining a metacarpophalangeal platform to support a palm of a user, the palmar support extending outward from the frame in a direction opposite the front portion of the finger cradle and hingeably coupled to the first side wall and the second side wall of the frame; and
a slide moveable with respect to the main body through the first opening, the slide including a head, the head having a predefined curvature.

10. The adjustable finger splint as recited in claim 9, wherein the slide releasably coupled to the main body.

11. The adjustable finger splint as recited in claim 9, wherein:
the main body defines at least one front surface to allow at least one healthy finger of a user to apply a first pressure to the adjustable finger splint; and
the slide includes at least one back surface to apply a second pressure to the slide, the second pressure in a direction opposite the first pressure.

12. The adjustable finger splint as recited in claim 9, wherein the slide platform includes one or more first notches and the slide includes one or more second notches, the first notches to engage the second notches during use.

13. The adjustable finger splint as recited in claim 9, wherein the front portion of the finger cradle is positioned within the first opening.

14. The adjustable finger splint as recited in claim 9, wherein the slide is movable with respect to and attached to the main body.

15. The adjustable finger splint as recited in claim 9, wherein a pad is positioned over the palmar support.

16. An adjustable finger splint comprising:
a main body including a frame, a back portion of a finger cradle, and a slide platform, the frame including a first side wall and a second side wall, the back portion of the finger cradle and the slide platform coupled between the first side wall and the second slide wall and defining a first opening;
a front portion of the finger cradle hingeably coupled to the first side wall and the second side wall of the frame, the front portion defining a second opening for receiving an injured finger; and
a palmar support hingeably coupled to the first side wall and the second side wall of the frame and defining a platform to support a palm of a user; and
a slide adjustable within the first opening and having a substantially linear body.

17. The adjustable finger splint as recited in claim 16, wherein the substantially linear body having a substantially horizontal top surface and at least one notch along a bottom surface, the at least one notch to engage with the slide platform and a head defining a curvature.

18. The adjustable finger splint as recited in claim 17, wherein the curvature is predefined.

19. The adjustable finger splint as recited in claim 17, wherein the slide includes a handle proximate to the head.

20. The adjustable finger splint as recited in claim 16, wherein the slide includes at least one slide rail.

* * * * *